United States Patent [19]

Beaudoin et al.

[11] Patent Number: 4,558,588
[45] Date of Patent: Dec. 17, 1985

[54] VIBRATING NEEDLE VISCOSITY METER

[75] Inventors: Paul Beaudoin, Villemandeur; Pierre Maronne, Chalette sur Loing, both of France

[73] Assignee: Societe Francaise de Services S.A., Villemandeur, France

[21] Appl. No.: 598,001

[22] Filed: Apr. 9, 1984

[30] Foreign Application Priority Data

Apr. 15, 1983 [FR] France ................ 83 06238

[51] Int. Cl.[4] .......................................... G01N 11/16
[52] U.S. Cl. ........................................................ 73/54
[58] Field of Search ..................................... 73/54, 59

[56] References Cited

U.S. PATENT DOCUMENTS

| 3,585,457 | 6/1971 | Zaander | 73/54 X |
| 3,710,614 | 1/1973 | Oppliger | 73/54 X |
| 3,903,732 | 9/1975 | Rork et al. | 73/54 |
| 4,166,381 | 9/1979 | Woo | 73/54 |

FOREIGN PATENT DOCUMENTS

| 899057 | 7/1944 | France | 73/54 |
| 851621 | 10/1960 | United Kingdom | 73/54 |

Primary Examiner—Stewart J. Levy
Assistant Examiner—Joseph W. Roskos
Attorney, Agent, or Firm—Larson and Taylor

[57] ABSTRACT

A viscosity meter comprises a straight metal rod having an end portion immersed in a fluid whose viscosity is determined. An intermediate portion of the rod is secured against movement and the other end portion is driven into transversal flexure oscillation by a coil. The coil is fed with an A.C. current at the natural frequency of the rod and the magnitude of the oscillation is measured.

9 Claims, 4 Drawing Figures

VIBRATING NEEDLE VISCOSITY METER

BACKGROUND AND SUMMARY OF THE INVENTION

The invention relates to viscosity meters of the type having a probe consisting of a straight needle which is adapted to be partially immersed in the fluid whose viscosity is to be measured. An intermediate portion of the needle is secured against movement to constitute a node and a portion of the needle remote from the immersed portion is provided with drive means for vibrating the needle transversally and with pick up means for delivering a signal representative of the amplitude of the vibration.

Viscosity meters of the above-defined type have been known for score of years (French No. 899,057). However, it was found that they are not suitable for use when a high accuracy is required or/and under circumstances where the viscosity may vary in a substantial range; consequently U-shaped probes rather than needles are used in the present day mechanical vibration viscosity meters (French No. 2,353,847). On the other hand, the increased complexity of the viscosity meters using a U-shaped probe represents a definite drawback.

The inventors have now found that the main deficiencies of the prior art needle type viscosity meters may in fact be removed if they are driven at the natural or resonance frequency of the needle; a difficulty then occurs, which is the variation of that frequency if the length of the immersed portion or the viscosity changes.

It is an object of the invention to provide a viscosity meter which retains the simplicity in design associated with a needle probe and substantially improves upon the accuracy, ease of use and range of operation of the prior art viscosity meters. It is an ancillary object to provide a viscosity meter whose response may be rendered substantially independent of the temperature variation in a broad range.

For that purpose, the needle is arranged to be vibrated by a stationary drive coil fed with an A.C. energizing current by an electric circuit connected to receive a signal from the pick up means at the vibrating frequency and including a feedback loop arranged to adjust the frequency of the A.C current at the natural frequency of the needle. The driving coil cooperates with a ferromagnetic element, typically a permanent magnet, carried by the needle.

Experience has shown that the response of a viscosity meter according to the invention is such that it is suitable for use in a very wide viscosity range, typically of from 1 to 10 cpo. An ancillary advantage is a life duration much increased as compared with the systems in which a probe is oscillated by a rotating cam and follower mechanism.

The needle will typically be secured in an end wall of a tube section whose opposite end is secured to a stationary plate. Then the vibration node will usually be between the ends of the tube section.

A measure of the viscosity of the fluid may be the magnitude of an electric signal delivered by the pick up means when a predetermined electrical power is applied to the drive coil. There exists pick up means (e.g. Hall elements) which provide a voltage which is in direct relation to the amount of vibration. In another embodiment, the electrical current applied to the drive means is adjusted for maintaining the amplitude of the output from the pick up means at a constant value and the power is measured for providing an indication of the viscosity.

The output from the pick up means, as well as the movement of the needle is approximately sine shaped. It is however preferable to deliver a square wave signal to the coil. It can be generated by amplifying and clipping the signal delivered by the pick up. With that approach, the vibration starts without an external action when power is applied.

SHORT DESCRIPTION OF THE DRAWINGS

DETAILED DESCRIPTON OF PREFERRED EMBODIMENTS

Figure 1:
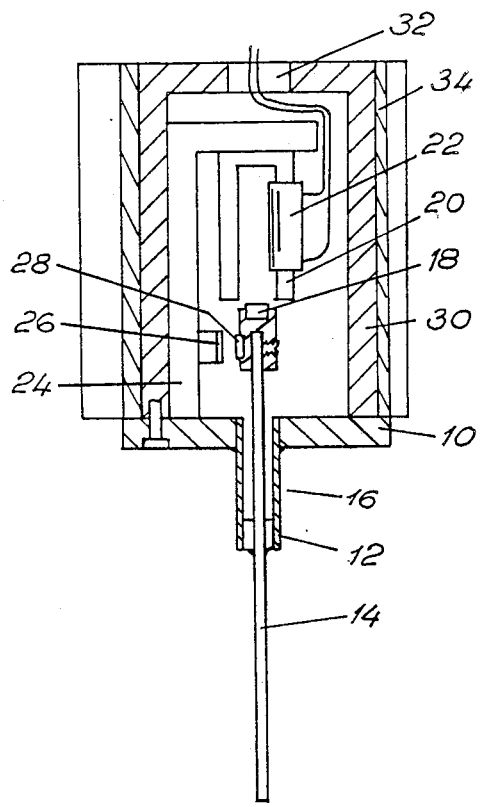
FIG. 1 is a schematic representation of the mechanical part of a viscosity meter according to an embodiment of the invention, in cross section along an axial plane.

Referring to FIG. 1, the mechanical parts of a viscosity meter comprise a base member 10 adapted to be secured onto a vessel or pipe containing the liquid or pasteous product whose viscosity is to be measured. A tube 12 of resilient metal (typically of stainless steel) is secured in an axial opening of the base member by appropriate means, for instance by force fitting and welding. A cylindrical needle 14 located along the axis of tube 12 projects from both ends of the tube 12. An intermediate portion of the needle is secured to an end portion of the tube remote from the base member. The rod may be secured by silver welding or electron beam welding. Means are provided for inducing a transversal flexure vibratory movement of the asembly 16 consisting of needle 14 and tube 12, which will thereafter be referred to as a rod. As shown, the means for driving the rod into oscillation comprises a permanent magnet 18 carried by the end of the rod which is remote from the portion adapted to be dipped into the product. Magnet 18 is located in the air gap of an electromagnet 20 having a driving coil 22 and carried by a frame 24 fixed to the base plate 10. The frame 24 also carries a displacement pick up 26, which may be a Hall probe cooperating with a magnet 28 carried by the needle. The magnets may be carried by a cap retained on the needle by a screw.

A protective casing 30 removably connected to the base plate 10 accomodates the mechanical components. The casing is formed with an opening through which the electrical components are connected to outside circuits. A finned sleeve 34 may be located around the casing for heat dispersal.

That arrangement makes it possible to use a simple construction. For instance, satisfactory results have been obtained with a stainless steel tube 12, 50 mm long and 0.25 mm thick, having an internal diameter of 4 mm. The length of the needle is 150 mm and the diameter 3 mm. The length or diameter of the needle will be selected at a value which is all the more greater as the viscosity is lower.

Figure 2:
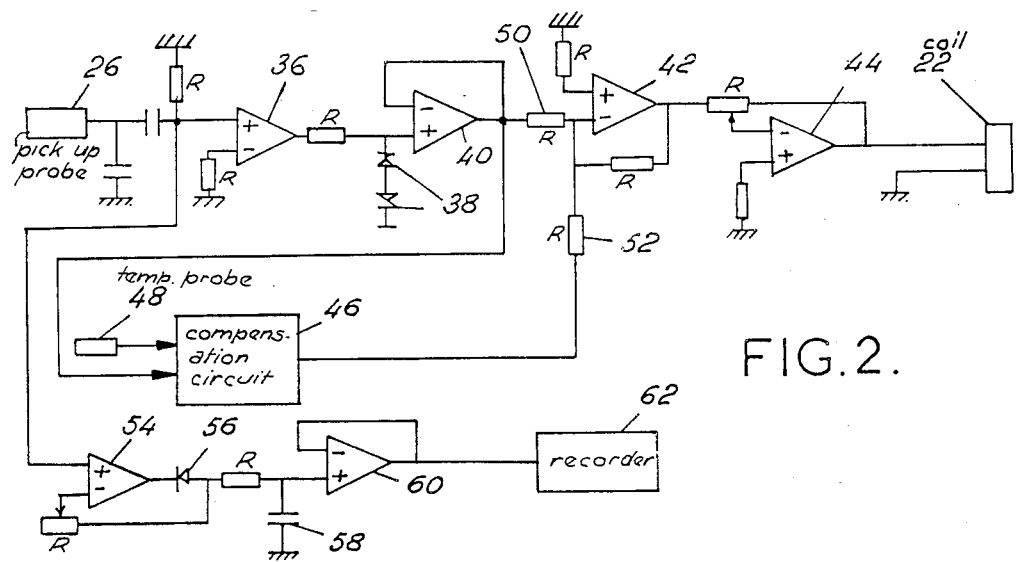
FIG. 2 is a block diagram of the energizing and measuring circuit of the viscosity meter of FIG. 1.

Referring to FIG. 2, there is illustrated a circuit which may be associated to the components of FIG. 1. The circuit of FIG. 2 is adapted to measure the amount of damping, and consequently the viscosity, by determining the magnitude of the oscillation when a constant driving power is applied. The circuit is associated with a D.C. power source (not shown). It delivers driving signals as square signals having a constant voltage as long as the operating temperature remains unchanged. If the operating termperature range is large, the circuit can include means for compensating the variation in resistance of the coil 22 as a function of temperature.

In a first embodiment, the pick up probe 26 consists of a Hall probe of a type which is currently available in the trade as a unit provided with its own temperature compensation circuit (Honeywell 92 SS 12-2 for instance). That probe delivers a sine shaped signal whose amplitude is in direct relation with that of the magnitude of the oscillation in a large range. The output of pick up probe 26 is applied to a measuring leg and a driving leg, which energizes coil 22.

The driving leg has an open loop operational amplifier 36 having a high gain. Two zener diodes 38 in opposed series relation connected between the output of amplifier 36 and ground clamp the signal for transforming it into square pulses. The zener diodes may be diodes having a triggering voltage of 5.1 Volt, for instance BZX 46C whose characteristics hardly vary with temperature.

The square signal is applied to a second operational amplifier 40 acting as follower. As illustrated in FIG. 2, amplifier 40 drives a summing amplifier 42 whose function will appear later. The output signal of amplifier 42 is applied to coil 22 through an operational amplifier 44 having an adjustable gain, which is used for manual gain adjustment.

As illustrated in FIG. 2, the curcuit has temperature compensation means for delivering square signals, at the output frequency of pick up probe 26, whose amplitude is variable in proportion to the temperature variation of the coil. The compensation means will not be described in detail, since they are quite conventional in nature and consist of operational amplifiers. One of the inputs of compensation means 46 receives a signal from the output of amplifier 40 and a temperature representative signal delivered by a probe 48 in close proximity to coil 22. The temperature probe 48 may for instance be a platinum resistance probe available from the firm THERMO-EST under reference K 201S.

A network of resistors 50, 52 connected to the inverting input of operational amplifier 42 is used for summing the output signals from the amplifier 40 and from the compensation means 46.

The measuring leg of the circuit includes an operational amplifier 54 connected to an output circuit having a rectifying diode 56 and a storage capacitor 58, whereby it operates as a rectifier-integrator. The D.C. voltage across capacitor 58 drives an impedance adaptation amplifier 60, connected as a follower. The output signal of amplifier 60 is applied to a recorder 62 which may be of any appropriate type.

It will be appreciated that the viscosity meter of the invention provides for excitation of the rod at its natural frequency, whatever the viscosity of the product. It has also attentent advantages: the amplitude of the oscillating movement is measured without mechanical contact; there is no appreciable wear of the driving mechanism; the system is not sensitive to perturbations of the A.C. network, since it uses a D.C. power source. It may operate in any angular position and it is of reduced bulk.

Since operation of the viscosity meter results from the description, it will not be analyzed in detail. The viscosity meter is so located that the unit consisting of the tube 12 and that part of needle 14 which projects from the tube is immersed in the product. Electrical power is applied. Operation occurs immediately, without any need for an outside excitation. The electronic part may be located at a distance. When the casing should be airtight, a grommet may be located in the opening of casing 30, with passages for the wires (two wires for coil 22, three wires for the Hall probe 26 and three wires for the temperature compensation probe).

Figure 3:
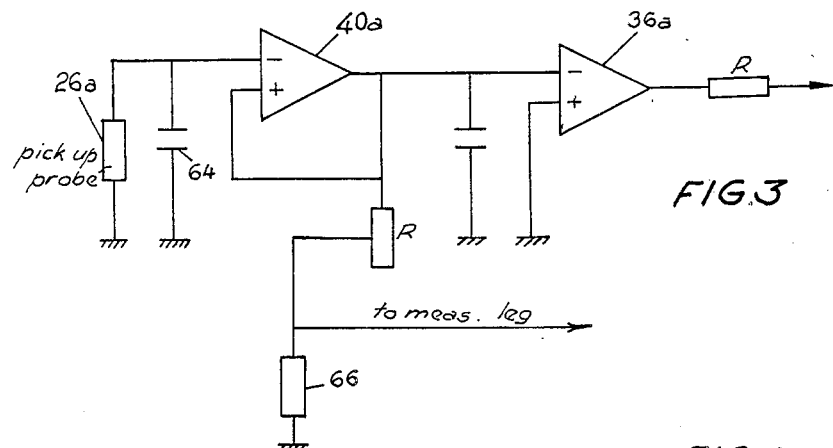
FIGS. 3 and 4 are block diagrams illustrating possible modifications of FIG. 2.

As already indicated, detectors other than a Hall probe may be used. Each particular type of detector will generally require a temperature compensation circuit which is particular to that detector. Referring to FIG. 3, there is shown the head portion of a circuit which makes use of an electromagnetic detector 26a. A capacitor 64 is connected across the detector for filtering purposes. The signal from detector 26a is applied to a closed loop operational amplifier 40a which drives an open loop operational amplifier 36a. Then, temperature compensation may use a coil 66 subjected to the same temperature as detector 26a and connected between a line toward the measuring leg and ground.

Figure 4:
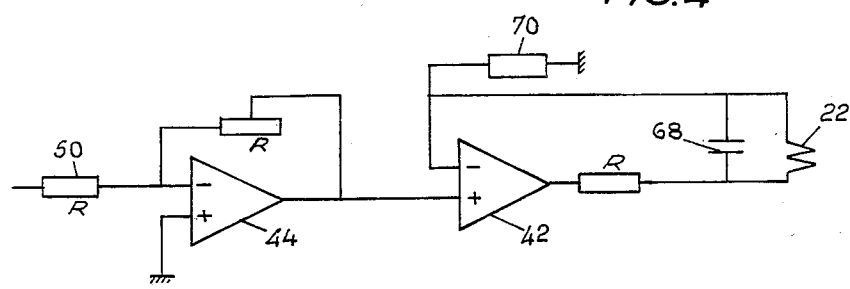

The thermal compensation circuit associated with the driving coil 22 may sometimes be omitted by operating it at a constant current value. Referring to FIG. 4, there is illustrated a circuit which may be substituted to the final portion of the energizing leg of FIG. 2. The drive coil 22 is inserted in a feedback loop of operational amplifier 42. A capacitor 68 across the terminals of coil 22 may be used for adjusting resonance. The feedback loop is connected to ground by a resistor 70 which increases safety by limiting the value of the current. The operational amplifiers may be of type LM 324 or TL 084. A Schmitt trigger (for instance 4093 of National Semiconductors) may be located upstream of amplifier 44 for shaping the signal.

We claim:

1. A viscosity meter for measuring the viscosity of a fluid comprising:
    stationary base means,
    a straight metal rod extending along a predetermined axis, having a first end portion adapted to be immersed in the fluid whose viscosity should be determined, a second end portion and an intermediate portion mechanically connected to said base means.
    drive means for maintaining said metal rod in transversal oscillation, having stationary coil means operatively associated with said second end portion and having circuit means for energizing said coil,
    and pick up means arranged to deliver an electrical signal representative of the amount of movement of said second end portion of said rod from a rest position,
    wherein said circuit means are connected to receive said electrical signal and to energize said drive means at a frequency which is equal to the natural oscillation frequency of the rod and is varied depending upon the viscosity of the fluid.

2. Viscosity meter according to claim 1, wherein said circuit comprises feedback means for maintaining the amplitude of oscillation of said rod at a constant value and means for measuring an electric power delivered to said coil by said circuit as an indication of the viscosity.

3. Viscosity meter according to claim 1, wherein said circuit comprises feedback means for maintaining an electric power delivered by said coil means at a constant value and means for measuring the magnitude of the output signal from the pick up means.

4. Viscosity meter according to claim 3, wherein said circuit includes:
a measuring leg including said means for measuring the magnitude of the output signal,
and an energization leg including said feedback means and having a high gain amplifier, clamping means connected to the output of said amplifier and delivering square pulses of a predetermined amplitude and at the frequency of said output signal and impedance matching and amplification means between said clamping means and said coil means.

5. Viscosity meter according to claim 4, wherein said impedance matching and amplification means include a summing amplifier connected to receive said square pulses of predetermined amplitude and a compensation signal consisting of square pulses at the frequency of said output signal and of an amplitude which is in relation with the temperature of said coil means.

6. A viscosity meter according to claim 4, wherein said means for measuring the magnitude of the output signal have an integrating amplifier connected to receive said output signal and delivering a D.C. signal whose value is in direct relation with said magnitude.

7. A viscosity meter according to claim 1, wherein said pick up means are a temperature compensated Hall probe.

8. A viscosity meter for measuring the viscosity of a fluid comprising:
stationary base means,
a straight metal rod extending along a predetermined axis, having a first end portion adapted to be immersed in a fluid whose viscosity should be determined, a second end portion carying a ferromagnetic element and an intermediate portion mechanically connected to said base means,
drive means for maintaining said metal rod in transversal flexure oscillation, having stationary coil means operatively associated with a magnet carried by said second end portion and having circuit means for energizing said coil,
and temperature compensated pick up means arranged to deliver an alternating electrical signal representative of the amount of movement of said ferromagnetic element,
wherein said circuit means are connected to receive said electrical signal and to energize said drive means at a frequency which is substantially equal to the natural transversal oscillation frequency of the rod.

9. A viscosity meter for measuring the viscosity of a fluid comprising:
stationary base means,
a straight metal tube extending along a predetermined axis, having a first end portion adapted to be immersed in a fluid whose viscosity should be determined and a second end portion secured to said base means,
a straight metal needle coaxial to said metal tube, having an external portion sealingly projecting through said first end portion of said metal tube and an internal end portion freely projecting through said second end portion out of said metal tube.
drive means for maintaining said metal needle in transversal flexure oscillation, having stationary coil means operatively associated with a ferromagnetic element carried by said second end portion and having circuit means for energizing said coil,
and pick up means arranged to deliver an alternating electrical signal representative of the amount of movement of said second end portion of said needle,
wherein said circuit means are connected to receive said electrical signal and to energize said drive means at a frequency which is substantially equal to the natural oscillation frequency of an assembly consisting of said tube and needle, whereby said assembly exhibits transversal flexure vibrations about a node located along said predetermined axis at a point between said first and second end portions.

* * * * *